United States Patent
Biato et al.

(10) Patent No.: US 11,234,907 B2
(45) Date of Patent: *Feb. 1, 2022

(54) COMPOSITION AND PROCESS FOR SHAPING OR ALTERING THE SHAPE OF HAIR

(71) Applicant: L'OREAL, Paris (FR)

(72) Inventors: Camila Maciel Biato, Rio de Janeiro (BR); Erika Alegrio Jarque Petali, Rio de Janeiro (BR); Bruno Sato, Rio de Janeiro (BR); Sintia Aguiar, Rio de Janeiro (BR)

(73) Assignee: L'OREAL, Paris (FR)

( * ) Notice: Subject to any disclaimer, the term of this patent is extended or adjusted under 35 U.S.C. 154(b) by 570 days.

This patent is subject to a terminal disclaimer.

(21) Appl. No.: 16/064,589

(22) PCT Filed: Dec. 23, 2015

(86) PCT No.: PCT/BR2015/050270
§ 371 (c)(1),
(2) Date: Jun. 21, 2018

(87) PCT Pub. No.: WO2017/106942
PCT Pub. Date: Jun. 29, 2017

(65) Prior Publication Data
US 2018/0369082 A1    Dec. 27, 2018

(51) Int. Cl.
*A61K 8/06* (2006.01)
*A61K 8/34* (2006.01)
(Continued)

(52) U.S. Cl.
CPC .......... *A61K 8/06* (2013.01); *A61K 8/24* (2013.01); *A61K 8/342* (2013.01); *A61K 8/375* (2013.01);
(Continued)

(58) Field of Classification Search
None
See application file for complete search history.

(56) References Cited

U.S. PATENT DOCUMENTS

2005/0048008 A1   3/2005 Gupta
2008/0025938 A1*  1/2008 Cassier .............. A61K 8/447
                                                    424/70.5

(Continued)

FOREIGN PATENT DOCUMENTS

EP    1466584 A2    10/2004
JP    2006076922 A   3/2006
(Continued)

OTHER PUBLICATIONS

Angus Chemical Company "AMP-Ultra PC Specialty Neutralizers" <http://latinamerica.in-cosmetics.com/_novadocuments/255482?v=636054135038200000> available May 2015; accessed Sep. 14, 2018 (Year: 2015).*

(Continued)

*Primary Examiner* — Nicole P Babson
(74) *Attorney, Agent, or Firm* — Polsinelli PC

(57) ABSTRACT

Disclosed herein is a composition in the form of an emulsion for shaping or altering the shape of hair, such as by straightening hair, wherein the composition contains a reducing agent, a neutralizing agent, at least two fatty substances, a nonionic surfactant selected from alkoxylated fatty alcohols (Continued)

| BEFORE TREATMENT | RINSE PROTOCOL | NON-RINSE PROTOCOL |
|---|---|---|
|  |  |  |
| Measurable attribute value: | 4.0 | 3.0 | and alkyl(ether)phosphates, optionally a quaternary ammonium compound, and water, wherein the pH of the composition ranges from about 2 to less than about 7. Also disclosed is a process for shaping or altering the shape of hair.

18 Claims, 1 Drawing Sheet

(51) Int. Cl.
      *A61K 8/55*       (2006.01)
      *A61Q 5/04*       (2006.01)
      *A61K 8/24*       (2006.01)
      *A61K 8/37*       (2006.01)
      *A61K 8/41*       (2006.01)
      *A61K 8/44*       (2006.01)
      *A61K 8/46*       (2006.01)
      *A61K 8/89*       (2006.01)
      *A61K 8/92*       (2006.01)
(52) U.S. Cl.
      CPC ............... *A61K 8/416* (2013.01); *A61K 8/44* (2013.01); *A61K 8/46* (2013.01); *A61K 8/556* (2013.01); *A61K 8/89* (2013.01); *A61K 8/922* (2013.01); *A61Q 5/04* (2013.01)

(56) References Cited

U.S. PATENT DOCUMENTS

| 2012/0121526 | A1 | 5/2012 | Hohenstein et al. |
| 2012/0183483 | A1* | 7/2012 | Misu ........................ A61K 8/86 424/70.2 |
| 2014/0261518 | A1* | 9/2014 | Savaides .................. A61Q 5/06 132/206 |

FOREIGN PATENT DOCUMENTS

| WO | 2011024300 A1 | 3/2011 |
| WO | 2015091743 A1 | 6/2015 |

OTHER PUBLICATIONS

Reiger, Martin M.. Harry's Cosmeticology, vols. I-II (8th Edition)—6.7 References. (pp. 109-128). Chemical Publishing Company Inc. (Year: 2000).*
International Search Report and Written Opinion dated Nov. 7, 2016 in corresponding PCT Application No. PCT/BR2015/050270.
International Preliminary Report on Patentability dated Jun. 26, 2018 for corresponding PCT Application No. PCT/BR2015/050270.

* cited by examiner

| BEFORE TREATMENT | RINSE PROTOCOL | NON-RINSE PROTOCOL |
|---|---|---|
|  | 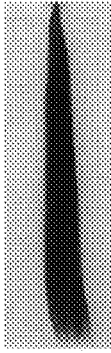 | 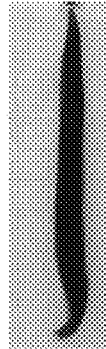 |
| Measurable attribute value: | 4.0 | 3.0 |

COMPOSITION AND PROCESS FOR SHAPING OR ALTERING THE SHAPE OF HAIR

CROSS-REFERENCE TO RELATED APPLICATIONS

This application is a national stage application (under 35 U.S.C. § 371) of PCT/BR2015/050270, filed Dec. 23, 2015, which is incorporated herein by reference in its entirety.

FIELD OF THE INVENTION

The present application relates to a composition and a process involving applying the composition in the form of an emulsion onto hair for shaping or altering the shape of the hair, for example, by straightening the hair, wherein the composition contains a reducing agent, a neutralizing agent, at least two fatty substances, an alkoylated fatty alcohol, optionally a quaternary ammonium compound, and water.

BACKGROUND OF THE INVENTION

Cosmetic and personal care products for use on keratinous substrates such as hair are available commercially in various forms, for example, as creams, lotions, gels, pastes, and powders. Regardless of the form, these products have to achieve and provide certain benefits and attributes such as efficaciousness, cosmeticity, desirable texture, stable formulations, and ease and convenience of use and application. Thus, in order to meet changing consumer needs and preferences, manufacturers of such products continuously seek to re-formulate and create new products with enhanced efficacy, while still remaining stable and safe to use. In addition, manufacturers continue to test the use of new raw materials and ingredients or new product forms that would help deliver the desired attributes and properties with respect to viscosity, texture, stability and efficacy.

One area where manufacturers are always seeking to improve in is in the area of hair cosmetic products such as those products designed to change the appearance, shape or configuration of hair. Examples of such hair cosmetic products are hair relaxers or hair straighteners which can relax or straighten curly or kinky hair, including wavy hair. Hair relaxers may either be applied in a hair salon by a professional or in the home by the individual consumer. Straightening or relaxing the curls of very curly hair may increase the manageability and ease of styling of such hair.

One type of composition that can be applied onto hair in order to change its shape and make it more manageable is an alkaline composition. Alkaline hair relaxing/straightening involves hydrolyzing the keratin of the hair with various alkaline agents, such as inorganic hydroxides, for instance sodium hydroxide, or organic hydroxides, such as guanidine hydroxide, or organic amines. Hair relaxing/straightening products that employ sodium hydroxide or potassium hydroxide are also called lye-based products and products that use other alkaline agents such as lithium hydroxide, calcium hydroxide, organic hydroxides and other non-hydroxide compounds, for example, organic amines, generally fall under the category of no-lye products.

Still, it is desirable to find alternatives to the alkaline lye- and no-lye-based products and process described above which can damage the hair by weakening and/or causing dryness of the hair fibers. However, the discovery of new compositions and processes for changing the shape of hair that impart less or minimal damage to hair, may pose challenges to manufacturers and formulators because the incorporation of new ingredients into the compositions may negatively impacting their performance, cosmetic attributes, and formulation stability. In addition, the alkalinity and/or pH is an important consideration for these products. New processes of treating and changing the shape of hair may also impact the performance of the compositions, processing times and quality of use.

The present invention provides a composition in the form of an emulsion for shaping or altering the shape of hair, such as by straightening the hair, containing a combination of a reducing agent, a neutralizing agent, at least two fatty substances, an alkoylated fatty alcohol, optionally a quaternary ammonium compound, and water wherein the composition is non-alkaline such that its pH ranges from about 2 to less than about 7. The present invention also provides a process for shaping or altering the shape of hair, such as by straightening the hair, in an easy and efficacious manner, the process comprising applying onto the hair, said composition, brushing the hair, heating the hair while optionally applying a smoothing action on the hair, and rinsing the hair with water or contacting the hair with an intermediate agent having a neutral pH and selected from a shampoo and/or a conditioner, followed by rinsing with water. The hair can be contacted with a shampoo having a neutral pH, then rinsed with water before the composition is applied onto the hair.

It was surprisingly and unexpectedly discovered that the composition of the present invention is stable and has a viscosity that corresponds to a non-drip, spreadable and homogeneous consistency that facilitates the ease of application of the composition onto hair fibers, thereby resulting in an effective process of shaping or altering the shape of hair. In addition, the process of the invention allows good straightening/relaxing of hair while at the same time limiting the degradation of hair and maintaining an appreciated working quality, especially without excessive vaporization of the composition at the time of straightening. The hair treatment process according to the invention also makes it possible to minimize the problems of breaking of the hair fibers. The composition and the process of the invention were also found to improve the physical properties of the hair, by durably reducing the volume of the hair and the frizziness effect.

BRIEF SUMMARY OF THE INVENTION

The present invention relates to a composition in the form of an emulsion for straightening hair comprising:
 (a) at least one reducing agent selected from thiol reducing agents, non-thiol reducing agents, and mixtures thereof;
 (b) at least one neutralizing agent;
 (c) at least two fatty substances comprising
  i. a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and
  ii. a second fatty substance selected from fatty alcohols;
 (d) at least one nonionic surfactant selected from alkoxylated fatty alcohols and alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;

(e) optionally, at least one quaternary ammonium compound; and (f) water;

wherein the pH of the composition ranges from 2 to less than 7

The present invention also relates to process for shaping hair or altering the shape of hair, the process comprising the steps of:

(a) applying onto the hair, the above-described composition;

(b) brushing the hair;

(c) heating the hair at a temperature of at least 40° C.; while optionally applying a smoothing action on the hair; and (d) rinsing the hair with water or contacting the hair with an intermediate agent having a neutral pH and selected from a shampoo and/or a conditioner, followed by rinsing with water.

The hair can be contacted with a shampoo having a neutral pH, then rinsed with water before the composition in (1) is applied onto the hair Methods of making the compositions of the present invention are also disclosed in this disclosure.

According to the present invention, the composition of the invention is preferably in the form of an emulsion, for example, oil-in-water emulsion and water-in-oil emulsion.

It is to be understood that both the foregoing general description and the following detailed description are exemplary and explanatory only, and are not restrictive of the invention.

BRIEF DESCRIPTION OF THE DRAWING

The Figure represents photographic images of hair samples, showing the straightening/shaping effects on hair imparted by the composition of the invention according to a rinsing protocol and a non-rinsing protocol.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−10% of the indicated number.

"Keratinous substrates" as used herein, include, but are not limited to skin, lips, and keratin or keratinous fibers such as hair and eyelashes.

"Volatile", as used herein, means having a flash point of less than about 100° C.

"Non-volatile", as used herein, means having a flash point of greater than about 100° C.

"Reducing agent" as used herein, means an agent capable of reducing the disulfide bonds of the hair.

"Active material" as used herein with respect to the percent amount of an ingredient or raw material, refers to 100% activity of the ingredient or raw material.

All numbers expressing pH values are to be understood as being modified in all instances by the term "about" which encompasses up to +/−3%.

The compositions and processes of the present invention can comprise, consist of, or consist essentially of the essential elements and limitations of the invention described herein, as well as any additional or optional ingredients, components, or limitations described herein or otherwise useful.

In one embodiment, the present invention relates to a composition in the form of an emulsion for straightening hair comprising:

(a) from about 1% to about 15% by weight of least one reducing agent selected from thiolactic acid, thioglycolic acid, and mixtures thereof;

(b) at least one neutralizing agent selected from aminomethyl propanol, monoethanolamine, and sodium hydroxide;

(c) at least two fatty substances comprising
  i. from about 1% to about 60% by weight of a first fatty substance selected from hydrocarbons, mineral oils, non-silicone synthetic oils, and mixtures thereof;
  ii. from about 2% to about 20% by weight of a second fatty substance selected from fatty alcohols (d) from about 2.5% to about 6% by weight of at least one nonionic surfactant selected from alkoxylated fatty alcohols and alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;

(e) water;

all weights being based on the total weight of the composition;

wherein when the at least one neutralizing agent is selected from aminomethyl propanol, the aminomethyl propanol is present in an amount of from about 0.1% to about 6.3% by weight;

wherein when the at least one neutralizing agent is selected from sodium hydroxide, the sodium hydroxide is present in an amount of from about 0.1% to about 4.1% by weight;

wherein when the at least one neutralizing agent is selected from monoethanolamine, the monoethanolamine is present in an amount of from about 0.1% to about 4.1% by weight;

wherein the pH of the composition ranges from 2 to less than 7; and wherein the composition is an emulsion.

In another embodiment, the present invention relates to an emulsion composition for straightening hair comprising:

(a) from about 4% to about 8% by weight of at least one reducing agent selected from thiolactic acid;

(b) at least one neutralizing agent;

(c) at least two fatty substances comprising
  i. from about 30% to about 50% by weight of mineral oil;
  ii. from about 5% to about 10% by weight of cetearyl alcohol;

(d) from about 2.5% to about 6% by weight of a mixture of PPG-5-Ceteth-10 phosphate, Ceteth-10 phosphate and Dicetyl phosphate.

(e) from about 1% to about 3% by weight of a mixture of polyuaterium-6 and polyquaternium-67; and (f) water;

all weights being based on the total weight of the composition;

wherein the pH of the composition ranges from 2 to less than 7.

In yet another embodiment, the present invention relates to an emulsion composition for straightening hair comprising:

(a) from about 4% to about 8% by weight of at least one reducing agent selected from thiolactic acid;

(b) at least one neutralizing agent;

(c) at least two fatty substances comprising
   i. from about 1% to about 5% by weight of mineral oil;
   ii. from about 5% to about 10% by weight of cetearyl alcohol;
(d) from about 2.5% to about 5% by weight of a mixture of PPG-5-Ceteth-10 phosphate, Ceteth-10 phosphate and Dicetyl phosphate;
(e) from about 1% to about 3% by weight of polyquaterium-6; and
(f) water;
all weights being based on the total weight of the composition;
wherein the pH of the composition ranges from 2 to less than 7.

In another embodiment, the present invention relates to an emulsion composition for straightening hair comprising:
(a) from about 4% to about 8% by weight of at least one reducing agent selected from thiolactic acid;
(b) at least one neutralizing agent;
(c) at least two fatty substances comprising
   i. from about 30% to about 50% by weight of mineral oil;
   ii. from about 5% to about 10% by weight of cetearyl alcohol;
(d) from about 2% to about 10% by weight of at least two alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof; and
(e) water;
all weights being based on the total weight of the composition;
wherein the pH of the composition ranges from 2 to less than 7.

In yet another embodiment, the present invention relates to an emulsion composition for straightening hair comprising:
(a) from about 4% to about 8% by weight of at least one reducing agent selected from thiolactic acid;
(b) at least one neutralizing agent;
(c) at least two fatty substances comprising
   i. from about 1% to about 5% by weight of mineral oil;
   ii. from about 5% to about 10% by weight of cetearyl alcohol;
(d) from about 1% to about 15% by weight of at least two alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof; and
(e) water;
all weights being based on the total weight of the composition;
wherein the pH of the composition ranges from 2 to less than 7.

In yet another embodiment, the present invention relates to an emulsion composition for straightening hair comprising:
(a) from about 4% to about 8% by weight of at least one reducing agent selected from thiolactic acid;
(b) at least one neutralizing agent selected from aminomethyl propanol, monoethanolamine and sodium hydroxide;
(c) at least two fatty substances comprising
   i. from about 1% to about 5% by weight of a first fatty substance selected from paraffin oils, petroleum jelly, liquid paraffin, polydecenes, hydrogenated polyisobutene, perfluoromethylcyclopentane, perfluoro-1,3-dimethylcyclohexane, dodecafluoropentane, mineral oil, hexane, dodecane, isohexadecane, isodecane, sunflower oil, maize oil, soya oil, cucurbit oil, grapeseed oil, sesame oil, hazelnut oil, apricot oil, macadamia oil, arara oil, sunflower oil, castor oil, avocado oil, jojoba oil, shea butter oil and mixtures thereof;
   ii. from about 5% to about 10% by weight of cetyl alcohol, stearyl alcohol cetearyl alcohol, oleyl alcohol, lauryl alcohol, behenyl alcohol, linoleyl alcohol, and mixtures thereof;
(d) from about 2.5% to about 5% by weight of at least one nonionic surfactant selected from alkoxylated fatty alcohols and alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof; and
(e) water;
all weights being based on the total weight of the composition;
wherein the pH of the composition ranges from 2 to less than 7.

In an embodiment, the present invention relates to a process for straightening hair, the process comprising the steps of:
(1) contacting hair with a shampoo having a neutral pH;
(2) rinsing the hair with water;
(3) applying onto the hair, a composition containing:
(a) from about 1% to about 15% by weight of least one reducing agent selected from thiolactic acid, thioglycolic acid, and mixtures thereof;
(b) at least one neutralizing agent selected from aminomethyl propanol, monoethanolamine and sodium hydroxide;
(c) at least two fatty substances comprising
   i. from about 1% to about 60% by weight of a first fatty substance selected from hydrocarbons, mineral oils, non-silicone synthetic oils, and mixtures thereof;
   ii. from about 2% to about 20% by weight of a second fatty substance selected from fatty alcohols
(d) from about 2.5% to about 5% by weight of at least one nonionic surfactant selected from alkoxylated fatty alcohols and alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;
(e) water;
all weights being based on the total weight of the composition;
wherein when the at least one neutralizing agent is selected from aminomethyl propanol, the aminomethyl propanol is present in an amount of from about 0.1% to about 6.3% by weight;
wherein when the at least one neutralizing agent is selected from sodium hydroxide, the sodium hydroxide is present in an amount of from about 0.1% to about 4.1% by weight;
wherein when the at least one neutralizing agent is selected from monoethanolamine, the monoethanolamine is present in an amount of from about 0.1% to about 4.1% by weight;
wherein the pH of the composition ranges from 2 to less than 7; and
wherein the composition is an emulsion.

(4) brushing the hair;

(5) heating the hair at a temperature of at least 40° C.; while optionally applying a smoothing action on the hair; and (6) rinsing the hair with water or contacting the hair with an intermediate agent having a neutral pH and selected from a shampoo and/or a conditioner, followed by rinsing with water.

Preferably, the above-described process comprises the steps of:

(1) First, contacting hair with a shampoo having a neutral pH;

(2) Second, rinsing the hair with water;

(3) Third, applying onto the hair, any one of the above-described compositions of the invention;

(4) Fourth, brushing the hair;

(5) Fifth, heating the hair at a temperature of at least 40° C.; while optionally applying a smoothing action on the hair; and (6) Sixth, heating the hair at a temperature of at least 40° C.; while optionally applying a smoothing action on the hair.

In certain embodiments, the heating step in any one of the above-described processes of the invention is preferably accomplished by use of device such as a heating flat iron device, a blow dryer, or a hair dryer. When a hair dryer or blow dryer is used, a brush or comb may be passed one or more times over or through the hair.

The heating step in any one of the above-described processes of the invention may also be accompanied by a smoothing action on the hair, preferably performed with a mechanical or physical device, for example, the plates of a flat iron or a hair brush.

In certain embodiments, the heating step in any one of the above-described processes is accomplished at a temperature higher than 100° C.

In certain embodiments, the composition in in any one of the above-described processes of the invention is allowed to remain on the hair for a predetermined amount of time sufficient to shape or alter the shape of the composition.

In preferred embodiments, the composition in any one of the above-described processes of the invention is a hair straightening composition. In yet other preferred embodiments, said hair straightening composition is allowed to remain on the hair for a predetermined amount of time sufficient as to achieve a desired degree of hair straightening.

The compositions in the above-described process are stable over time, that is, they do not exhibit phase separation and they can be stored for several months without modification and with very little change or fluctuation in the viscosity and/or rheology and pH of the composition.

It was surprisingly and unexpectedly discovered that the application of the compositions of the present invention, resulted in effectively shaped or straightened hair.

It was also surprisingly and unexpectedly discovered that the composition of the invention was stable over time and had a smooth, non-drip, and homogenous texture/consistency and effectively shaped or straightened hair.

The non-drip consistency of the compositions of the present invention is desirable because it helps the compositions to remain on the hair for a predetermined amount of time as to achieve the desired shape of the hair or desired degree of straightening of the hair.

Reducing Agent

The present invention employs at least one reducing agent selected from thiol or non-thiol reducing agents.

Thiol reducing agents which can be used in the composition of the invention include thiol reducing agents selected from thiolactic acid, thioglycolic acid, cysteine, cysteamine, homocystine, glutathione, thioglycerol, thiomalic acid, 2-mercaptopropionic acid, 3-mercaptopropionic acid, thio diglyco I, 2-mercaptoethanol, dithiothreitol, thioxanthine, thiosalicylic acid, thiopropionic acid, lipoic acid, N-acetyl-cysteine, their salts thereof, and mixtures thereof.

Non-thiol reducing agents which can be used in the composition of the invention include in particular alkali metal, alkaline-earth metal sulfites, hydrides or phosphines, and mixtures thereof.

In some embodiments, the reducing agent or agents used in the composition of the invention are thiol reducing agents, more particularly thioglycolic acid and thiolactic acid or their salts thereof, especially alkali metal, alkaline-earth metal or ammonium salts, cysteine, and mixtures thereof.

In yet other embodiments, the reducing agent used in the composition of the invention is chosen from thiolactic acid, thioglycolic acid, and mixtures thereof In certain embodiments, the reducing agent used in the composition of the invention is thiolactic acid.

In other embodiments, the reducing agent used in the composition of the invention is thioglycolic acid.

In yet other embodiments, the reducing agent used in the composition of the invention comprises thiolactic acid and thiolgycolic acid.

The at least one reducing agent can be employed in the composition of the present invention in an amount of from about 1% to about 15% by weight, preferably from about 3% to about 10% by weight, more preferably from about 4% to about 8% by weight, based on the total weight of the composition, including all ranges and subranges therebetween.

In certain embodiments, the at least one reducing agent is selected from thiolactic acid and is employed in the composition of the present invention in an amount of about 1%, or about 2%, of about 3%, or about 4%, or about 5%, of about 5.5%, or about 6%, or about 6.5%, or about 7%, or about 7.5%, or about 8%, or about 9%, or about 10% by weight, based on the total weight of the composition.

Fatty Substances

The present invention employs at least two fatty substances.

The term "fatty substance" means an organic compound that is insoluble in water at ordinary room temperature (25 degrees centigrade) and at atmospheric pressure (760 mmHg) (solubility of less than 5 percent, preferably 1 percent and even more preferentially 0.1 percent). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

First Fatty Substance

The present invention employs a first fatty substance selected from alkanes, esters of fatty acid, esters of fatty alcohol, hydrocarbons, silicones, non-silicone waxes, mineral oils, vegetable oils, non-silicone synthetic oils, and mixtures thereof.

The fatty substances are especially chosen from $C_6$-$C_{16}$ hydrocarbons, hydrocarbons containing more than 16 carbon atoms and in particular alkanes, oils of animal origin, oils of plant origin, glycerides or fluoro oils of synthetic origin, fatty acid and/or fatty alcohol esters, non-silicone waxes and silicones.

It is recalled that, for the purposes of the invention, the fatty esters and fatty acids more particularly contain one or more linear or branched, saturated or unsaturated hydrocarbon-based groups comprising 6 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear, branched or possibly cyclic. Mention may be made, by way of example, of hexane, dodecane or isoparaffins, such as isohexadecane or isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, jojoba oil, shea butter oil and caprylic/capric acid triglycerides, for instance those sold by the company Stearineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The wax(es) that may be used in the anhydrous cosmetic composition (I) are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of a fatty acid and/or of a fatty alcohol, which are advantageously different from the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates, such as isopropyl, butyl, cetyl, 2-octyldodecyl, myristyl or stearyl myristate; hexyl stearate; butyl stearate; isobutyl stearate; dioctyl malate; hexyl laurate or 2-hexyldecyl laurate.

Still within the context of this alternative form, use may also be made of esters of $C_4$-$C_{22}$ di- or tricarboxylic acids and of $C_1$-$C_{22}$ alcohols and esters of mono-, di- or tricarboxylic acids and of di-, tri-, tetra- or pentahydroxy $C_2$-$C_{26}$ alcohols.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition can also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$ and preferably $C_{12}$-$C_{22}$ fatty acids. If they are unsaturated, these compounds can comprise from one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by Amerchol, which is a methylglucose dioleate.

Mention may also be made, by way of examples of esters or mixtures of esters of sugar and of fatty acid, of:

the products sold under the names F160, F140, F110, F90, F70 and SL40 by Crodesta, respectively denoting sucrose palmitate/stearates formed of 73 percent monoester and 27 percent di- and triester, of 61 percent monoester and 39 percent di-, tri- and tetraester, of 52 percent monoester and 48 percent di-, tri- and tetraester, of 45 percent monoester and 55 percent di-, tri- and tetraester, and of 39 percent monoester and 61 percent di-, tri- and tetraester, and sucrose monolaurate;

the products sold under the name Ryoto Sugar Esters, for example referenced B370 and corresponding to sucrose behenate formed of 20 percent monoester and 80 percent diester, triester and polyester;

the sucrose monopalmitate/stearate-di palmitate/stearate sold by Goldschmidt under the name Tegosoft® PSE.

The silicones that can be used in the cosmetic composition of the present invention are volatile or non-volatile, cyclic, linear or branched silicones, which are unmodified or modified with organic groups, having a viscosity from $5 \times 10^{-6}$ to 2.5 m$^2$/s at 25 degrees centigrade, and preferably $1 \times 10^{-5}$ to 1 m$^2$/s.

The silicones which can be used in accordance with the invention can be provided in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in more detail in Walter Noll's "Chemistry and Technology of Silicones" (1968), Academic Press. They can be volatile or non-volatile.

When they are volatile, the silicones are more particularly chosen from those having a boiling point of between 60 degrees centigrade and 260 degrees centigrade, and more particularly still from:

(i) cyclic polydialkylsiloxanes comprising from 3 to 7 and preferably from 4 to 5 silicon atoms. They are, for example, octamethylcyclotetrasiloxane, sold in particular under the name Volatile Silicone® 7207 by Union Carbide or Silbione® 70045 V2 by Rhodia, decamethylcyclopentasiloxane, sold under the name Volatile Silicone® 7158 by Union Carbide and Silbione® 70045 V5 by Rhodia, and mixtures thereof.

Mention may also be made of cyclocopolymers of the dimethylsiloxane/methylalkylsiloxane type, such as Volatile Silicone® FZ 3109, sold by Union Carbide, having the formula:

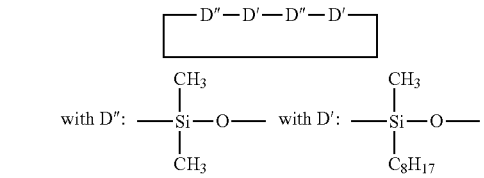

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25 degrees centigrade An example is decamethyltetrasiloxane sold in particular under the name SH 200 by the company Toray Silicone. Silicones coming within this category are also described in the paper published in Cosmetics and Toiletries, Vol. 91, January 76, pp. 27-32, Todd and Byers, Volatile Silicone Fluids for Cosmetics.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25 degrees centigrade according to Standard ASTM 445 Appendix C.

Mention may be made, among these polydialkylsiloxanes, without implied limitation, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from Dow Corning, such as DC200 having a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

Mention may also be made, in this category of polydialkylsiloxanes, of the products sold under the names Abil Wax® 9800 and 9801 by Goldschmidt, which are polydi (C$_1$-C$_{20}$)alkylsiloxanes.

The silicone gums which can be used in accordance with the invention are in particular polydialkylsiloxanes and preferably polydimethylsiloxanes having high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures, such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;

the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;

the mixtures of two PDMSs with different viscosities, and more particularly of a PDMS gum and a PDMS oil, such as the product SF 1236 from General Electric. The product SF 1236 is the mixture of a gum SE 30 defined above having a viscosity of 20 $m^2/s$ and of an oil SF 96 with a viscosity of $5 \times 10^{-6}$ $m^2/s$. This product preferably comprises 15 percent of gum SE 30 and 85 percent of an oil SF 96.

The organopolysiloxane resins which can be used in accordance with the invention are crosslinked siloxane systems including the following units:

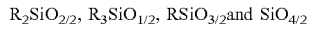

in which R represents an alkyl having from 1 to 16 carbon atoms. Among these products, those that are particularly preferred are those in which R denotes a lower $C_1$-$C_4$ alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones which can be used in accordance with the invention are silicones as defined above comprising, in their structure, one or more organofunctional groups attached via a hydrocarbon group.

In addition to the silicones described above, the organomodified silicones can be polydiarylsiloxanes, in particular polydiphenylsiloxanes, and polyalkylarylsiloxanes functionalized by the abovementioned organo functional groups.

The polyalkylarylsiloxanes are chosen in particular from linear and/or branched polydimethyl/methylphenylsiloxanes and polydimethyl/diphenylsiloxanes with a viscosity ranging from $1 \times 10^{-5}$ to $5 \times 10^{-2}$ $m^2/s$ at 25 degrees centigrade Among these polyalkylarylsiloxanes, examples that may be mentioned include the products sold under the following names:

Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Mention may be made, among the organomodified silicones, of polyorganosiloxanes comprising:

polyethyleneoxy and/or polypropyleneoxy groups optionally comprising $C_6$-$C_{24}$ alkyl groups, such as the products named dimethicone copolyol sold by Dow Corning under the name DC 1248 or the oils Silwet® L 722, L 7500, L 77 and L 711 by Union Carbide, and the ($C_{12}$)alkyl methicone copolyol sold by Dow Corning under the name Q2 5200;

substituted or unsubstituted amino groups, such as the products sold under the names GP 4 Silicone Fluid and GP 7100 by Genesee or the products sold under the names Q2 8220 and Dow Corning 929 or 939 by Dow Corning. The substituted amino groups are in particular $C_1$-$C_4$ aminoalkyl groups;

alkoxylated groups, such as the product sold under the name Silicone Copolymer F-755 by SWS Silicones, and Abil Wax® 2428, 2434 and 2440 by Goldschmidt.

Preferably, the first fatty substances do not comprise any $C_2$-$C_3$ oxyalkylene units or any glycerol units. Preferably, the first fatty substances are not salified fatty acids or soaps, which are water-soluble compounds.

The first fatty substances are advantageously chosen from $C_6$-$C_{16}$ hydrocarbons, hydrocarbons containing more than 16 carbon atoms and in particular alkanes, oils of plant origin, fatty acid and/or fatty alcohol esters, and silicones, or mixtures thereof.

Preferably, the first fatty substance is an oil (a compound that is liquid at a temperature of 25 degrees centigrade and at atmospheric pressure).

Preferably, the first fatty substance is chosen from mineral oil, $C_6$-$C_{16}$ alkanes, polydecenes, liquid fatty acid and/or fatty alcohol esters or their mixtures.

Better still, the fatty substance is chosen from mineral oil, $C_6$-$C_{16}$ alkanes or polydecenes.

Most preferably, the first fatty substance is chosen from paraffin oils, petroleum jelly, liquid paraffin, polydecenes, hydrogenated polyisobutene, perfluoromethylcyclopentane, perfluoro-1,3-dimethylcyclohexane, mineral oil, dodecafluoropentane, hexane, dodecane, isohexadecane, isodecane, sunflower oil, maize oil, soya oil, cucurbit oil, grapeseed oil, sesame oil, hazelnut oil, apricot oil, macadamia oil, arara oil, sunflower oil, castor oil, avocado oil, jojoba oil, shea butter oil and mixtures thereof.

The first fatty substance can be employed in the composition of the present invention in an amount of from about 0.1% to about 70% by weight, preferably from about 0.5% to about 65% by weight, more preferably from about 1% to about 60% by weight, more preferably from about 1.5% to about 55% by weight, more preferably from about 1.75% to about 50% by weight, more preferably from about 2% to about 45% by weight, based on the total weight of the composition, including all ranges and subranges therebetween.

In certain embodiments, the first fatty substance is selected from mineral oil and is employed in the composition of the present invention in an amount of about 1%, or about 2%, of about 3%, or about 4%, or about 5%, or about 5.5%, or about 6%, or about 6.5%, or about 7%, or about 7.5%, or about 8%, or about 9%, or about 10% by weight, based on the total weight of the composition.

In other embodiments, the first fatty substance is selected from mineral oil and is employed in the composition of the present invention in an amount of about 40%, or about 41%, of about 42%, or about 43%, or about 43.5%, or about 44%, or about 44.5%, or about 45%, or about 46%, or about 47%, or about 48%, or about 49%, or about 50% by weight, based on the total weight of the composition.

Second Fatty Substance

The present invention employs a second fatty substance selected from fatty alcohols.

The fatty alcohols that may be used in the composition may be chosen from alcohols of formula R'OH, in which R' denotes a saturated or unsaturated, linear or branched radical, comprising from 6 to 40 carbon atoms and more particularly from 8 to 30 carbon atoms. Examples that may be mentioned include cetyl alcohol, stearyl alcohol and the mixture thereof (cetearyl alcohol), octyldodecanol, 2-butyloctanol, 2-hexyldecanol, 2-undecylpentadecanol, oleyl alcohol, lauryl alcohol, behenyl alcohol and linoleyl alcohol.

The second fatty substance can be employed in the composition of the present invention in an amount of from about 0.5% to about 30% by weight, preferably from about 1% to about 25% by weight, more preferably from about 2% to about 20% by weight, more preferably from about 2.5% to about 15% by weight, more preferably from about 2.75% to about 12% by weight, more preferably from about 3% to about 10% by weight, based on the total weight of the composition, including all ranges and subranges therebetween.

In certain embodiments, the second fatty substance is selected from cetearyl alcohol and is employed in the composition of the present invention in an amount of about 1%, or about 2%, of about 3%, or about 4%, or about 5%, or about 5.5%, or about 6%, or about 6.5%, or about 7%, or about 7.5%, or about 8%, or about 9%, or about 10% by weight, based on the total weight of the composition.

Neutralizing Agent

Suitable neutralizing agents may be selected from alkali metal carbonates, alkali metal phosphates, organic amines, hydroxide base compounds, and mixtures thereof, particularly from organic amines, alkali metal hydroxides, alkali earth metal hydroxides, and mixtures thereof.

Organic amines may be selected from amino-2-methyl-1-propanol (or aminomethyl propanol), ethylamines, ethyleneamines, alkanolamines, cyclic amines and other cyclic compounds, saturated or unsaturated, having one or more nitrogen atoms within the ring, and mixtures thereof.

The organic amines may be chosen from the ones having a pKb at 25□ of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

The at least one neutralizing agent may be chosen from at least one organic amine such as at least one alkanolamine. Particularly preferred alkanolamines are 2-amino-2-methyl-1-propanol (aminomethyl propanol), ethanolamine (also known as monoethanolamine or MEA), triethanolamine, and mixtures thereof. An even more particularly preferred alkanolamine is ethanolamine.

According to at least one embodiment, the at least one neutralizing agent is chosen from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

According to another preferred embodiment, the at least one neutralizing agent is chosen from aminomethyl propanol, sodium hydroxide, lithium hydroxide, calcium hydroxide, monoethanolamine, and mixtures thereof.

In one preferred embodiment, the at least one neutralizing agent is selected from aminomethyl propanol and is present in an amount of from about 0.1% to about 6.3% by weight, preferably from about 0.2% to about 5.5% by weight, more preferably from about 0.3% to about 5% by weight, even more preferably from about 0.3% to about 4.6% by weight, based on the total weight of the composition, including all ranges and subranges there between.

In certain embodiments, the at least one neutralizing agent selected from aminomethyl propanol is employed in the compositions of the present invention in an amount of about 0.1%, 0.3%, 0.4%, 0.5%, 0.6%, 0.7%, 0.8%, 0.9%, 1%, 1.3%, 1.4%, 1.5%, 1.75%, 2%, 2.3%, 2.4%, 2.5%, 2.75%, or 3%, 3.3%, 3.5%, 3.75%, 4%, 4.3%, 4.5%, 4.6%, by weight, based on the total weight of the composition.

In another preferred embodiment, the at least one neutralizing agent is selected from sodium hydroxide and is present in an amount of from about 0.1% to about 4.1% by weight, preferably from about 0.15% to about 3.5% by weight, more preferably from about 0.2% to about 3% by weight, even more preferably from about 1% to about 3% by weight, based on the total weight of the composition, including all ranges and subranges therebetween.

In certain embodiments, the at least one neutralizing agent selected from sodium hydroxide is employed in the compositions of the present invention in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, about 2.3%, 2.4%, 2.5%, 2.6%, 2.7%, 2.8%, 2.9%, 3%, based on the total weight of the composition.

In yet another preferred embodiment, the at least one neutralizing agent is selected from monoethanolamine and is present in an amount of from about 0.1% to about 6.3% by weight, preferably from about 0.2% to about 5.5% by weight, more preferably from about 0.3% to about 5% by weight, even more preferably from about 0.3% to about 4.6% by weight, based on the total weight of the composition, including all ranges and subranges there between.

In certain embodiments, the at least one neutralizing agent selected from monoethanolamine is employed in the compositions of the present invention in an amount of about 0.1%, 0.3%, 0.4%, 0.5%, 0.6%, 0.7%, 0.8%, 0.9%, 1%, 1.3%, 1.4%, 1.5%, 1.75%, 2%, 2.3%, 2.4%, 2.5%, 2.75%, or 3%, 3.3%, 3.5%, 3.75%, 4%, 4.3%, 4.5%, 4.6%, by weight, based on the total weight of the composition.

Nonionic Surfactant

The compositions according to various embodiments of the disclosure also comprise at least one nonionic surfactant chosen from alkoxylated fatty alcohols and alkyl(ether) phosphates.

"Alkoxylated fatty alcohol" as used herein means a compound having at least one fatty portion (8 carbon atoms or more) and at least one alkoxylated portion ($-(CH_2)_nO-$, where n is an integer from 1 to 5, preferably 2 to 3). According to particularly preferred embodiments, the alkoxylated fatty alcohols of the present invention can be used as non-ionic surfactants, if desired. In this regard, the alkoxylated fatty alcohols of the present invention preferably have an HLB (hydrophilic-lipophilic balance) value from 1-20, including all ranges and subranges therebetween, with HLB values ranging from 1 to 5 (particularly 3 to 5) or from 15-20 (particularly 16 to 18) being most preferred.

Preferably, the alkoxylated fatty alcohol can be chosen from di-alkyl, tri-alkyl- and combinations of di-alkyl and tri-alkyl substituted ethoxylated polymers. They can also be chosen from mono-alkyl, di-alkyl, tri-alkyl, tetra-alkyl substituted alkyl ethoxylated polymers and all combinations thereof. The alkyl group can be saturated or unsaturated, branched or linear and contain a number of carbon atoms preferably from about 12 carbon atoms to about 50 carbon atoms, including all ranges and subranges therebetween, for example, 20 to 40 carbon atoms, 22 to 24 carbon atoms, 30 to 50 carbon atoms, and 40 to 60 carbon atoms. Most preferably, the fatty portion contains a mixture of compounds of varying carbon atoms such as, for example, C20-C40 compounds, C22-C24 compounds, C30-050 compounds, and C40-C60 compounds.

Preferably, the alkoxylated portion of the alkoxylated fatty alcohols of the present invention contain 2 or more alkoxylation units, preferably from 10 to 200 alkoxylation units, preferably from 20 to 150 alkoxylation units, and preferably from 25 to 100 alkoxylation units, including all ranges and subranges therebetween. Also preferably, the alkoxylation units contain 2 carbon atoms (ethoxylation units) and/or 3 carbon atoms (propoxylation units).

The amount of alkoxylation can also be determined by the percent by weight of the alkoxylated portion with respect to the total weight of the compound. Suitable weight percentages of the alkoxylated portion with respect to the total weight of the compound include, but are not limited to, 10 percent to 95 percent, preferably 20 percent to 90 percent, including all ranges and subranges therebetween with 75 percent to 90 percent (particularly 80 percent to 90 percent) or 20 percent to 50 percent being preferred.

Preferably, the alkoxylated fatty alcohols of the present invention have a number average molecular weight (Mn) greater than 500, preferably from 500 to 5,000, including all ranges and subranges therebetween such as, for example, Mn of 500 to 1250 or an Mn of 2,000 to 5,000.

The alkyl substitution of the alkoxylated fatty alcohol can include mono-alkyl, di-alkyl, tri-alkyl and tetra-alkyl substitution of the polymer and combinations thereof. Suitable examples of mono alkyl substituted polymers include: Steareth-100 available as Brij 700 from Uniqema Inc., Pareth alcohols available as Performathox 450, 480 and 490 available from New Phase Technologies, Inc. Suitable examples of di-alkyl substituted polymers include PEG 120 methyl glucose dioleate available as Glutamate DOE-120 and Glucamate DOE-120 both from Chemron Corporation. Suitable examples of tri-alkyl substituted polymers include PEG 120 methyl glucose trioleate available as Glucamate LT from Chemron Corporation. Suitable examples of tetra-alkyl substituted polymers include PEG 150 pentaerythrityl tetrastearate available as Crothix from Croda Corporation.

Suitable alkoxylated fatty alcohols for use in the present invention include, but are not limited to, alkoxylated C20-C40 fatty alcohols sold under the PERFORMATHOX® name by New Phase Technologies such as, for example, PERFORMATHOX® 420 ETHOXYLATE (Mn=575; 20 percent by weight ethoxylation), PERFORMATHOX® 450

ETHOXYLATE (Mn=920; 50 percent by weight ethoxylation), PERFORMATHOX® 480 ETHOXYLATE (Mn=2300; 80 percent by weight ethoxylation), PERFORMATHOX® 490 ETHOXYLATE (Mn=4600; 90 percent by weight ethoxylation), PERFORMATHOX® 520 ETHOXYLATE (Mn=690; 20 percent by weight ethoxylation), and PERFORMATHOX® 550 ETHOXYLATE (Mn=1100; 50 percent by weight ethoxylation).

Suitable alkyl(ether)phosphates include, but are not limited to, alkoxylated alkyl phosphate esters and alkyl phosphate esters corresponding to a mono-ester of formula (I) and salts thereof:

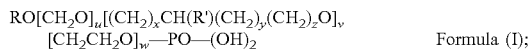

$$RO[CH_2O]_u[(CH_2)_xCH(R')(CH_2)_y(CH_2)_zO]_v[CH_2CH_2O]_w\text{—}PO\text{—}(OH)_2 \quad \text{Formula (I);}$$

a di-ester corresponding to formula (II) and salts thereof:

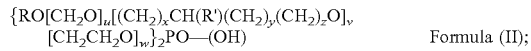

$$\{RO[CH_2O]_u[(CH_2)_xCH(R')(CH_2)_y(CH_2)_zO]_v[CH_2CH_2O]_w\}_2PO\text{—}(OH) \quad \text{Formula (II);}$$

a tri-ester corresponding to formula (III):

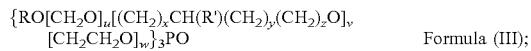

$$\{RO[CH_2O]_u[(CH_2)_xCH(R')(CH_2)_y(CH_2)_zO]_v[CH_2CH_2O]_w\}_3PO \quad \text{Formula (III);}$$

and combinations thereof, wherein:

R is a hydrocarbon radical containing from 6 to 40 carbon atoms;

u, v and w, independently of one another, represent numbers of from 0 to 60;

x, y and z, independently of one another, represent numbers of from 0 to 13;

R' represents hydrogen, alkyl, the sum of x+y+z being ?0. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas (I), (II) and (III), R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group; u, v, w, independently of one another, is preferably a number from 2 to 20, more preferably a number from 3 to 17 and most preferably a number from 5 to 15;

x, y, z, independently of one another, is preferably a number from 2 to 13, more preferably a number from 1 to 10 and most preferably a number from 0 to 8.

In general, the lower the number of carbon atoms in the R group of the phosphate esters, the more irritating to the skin and the less soluble in water the phosphate ester becomes. In contrast, the higher the number of carbon atoms in the R group, the milder to the skin and the thicker and more waxy the resultant product becomes. Accordingly, for best results, R should have from 12 to 18 carbon atoms.

Particularly preferred alkoxylated alkyl phosphate esters for use in the present invention are PPG-5-Ceteth-10 phosphate (CRODAFOS SG®), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda. Particularly preferred alkyl phosphate esters are Cetyl phosphate (Hostaphat CC 100), Stearyl phosphate (Hostaphat CS 120) from Clariant.

In the present invention, the at least one nonionic surfactant chosen from alkoylated fatty alcohols can be employed in the composition of the present invention in an amount of from about 0.1% to about 20% by weight, preferably from about 0.5% to about 18% by weight, preferably from about 1% to about 15% by weight, preferably from about 1.5% to about 12%, preferably from about 2% to about 10% by weight, preferably from about 2.25% to about 8% by weight, preferably from about 2.5% to about 6% by weight, and most preferably from about 2.5% to about 5% by weight, based on the weight of the composition as a whole, including all ranges and subranges within these ranges.

In certain embodiments, the at least one nonionic surfactant chosen from alkoylated fatty alcohols and alkyl(ether) phosphates is selected from PPG-5-Ceteth-10 phosphate, Ceteth-10 phosphate and Dicetyl phosphate, and is employed in the composition of the present invention in an amount of about 1%, or about 2%, or about 2.25%, or about 2.5%, or about 2.75%, or about 3%, or about 3.25%, or about 3.5%, or about 3.75%, or about 4%, or about 4.25%, or about 4.5%, or about 4.75%, or about 5%, or about 5.25%, or about 5.5% by weight, based on the total weight of the composition.

Quaternary Ammonium Compound

The compositions according to the present invention may also comprise at least one quaternary ammonium compound. This compound may be in the form of a cationic polymer or in the form of a quaternary ammonium salt.

The quaternary ammonium compound may be chosen from cationic associative polymers comprising, in their structure, a pendent or terminal hydrophobic chain, for example of alkyl or alkenyl type, containing from 10 to 30 carbon atoms.

The quaternary ammonium compound of the compositions can also be chosen from, for example:

(1) homopolymers and copolymers derived from acrylic or methacrylic esters or amides, examples of which are:

copolymers of acrylamide and of dimethylaminoethyl acrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl acrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylaminopropylmethacrylamide copolymers such as the product sold under the name GAFQUAT HS 100 by the company ISP, and cross-linked polymers of methacryloyloxy($C_1$-$C_4$)alkyltri($C_1$-$C_4$) alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide. In at least one embodiment, a crosslinked acrylamide/methacryloyloxyethyltrimethylammonium chloride copolymer (20/80 by weight) in the form of a dispersion containing 50 percent by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50 percent by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) non-cellulose cationic polysaccharides, such as guar gums containing trialkylammonium cationic groups. Such products are sold, for example, under the trade names JAGUAR C13S , JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) the polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) quaternary diammonium polymers.

(9) polyquaternary ammonium polymers; examples that may be mentioned include the products MIRAPOL A 15, MIRAPOL AD1, MIRAPOL AZ1 and MIRAPOL 175 sold by the company Miranol.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly (vinylamine/vinylamide)s.

(12) cationic polyurethane derivatives, for example those of elastic nature formed from the reaction:

(a1) of at least one cationic unit resulting from at least one tertiary or quaternary amine bearing at least two reactive functions containing labile hydrogen, (a2) of at least one mixture of at least two different nonionic units bearing at least two reactive functions containing labile hydrogen, for instance chosen from hydroxyl groups, primary or secondary amine groups, and thiol groups, and (b) of at least one compound comprising at least two isocyanate functions.

(13) Other quaternary ammonium compound that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful quaternary ammonium compound in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred quaternary ammonium compound of the present invention include SOFTCAT POLYMER SL-100 (Polyquaternium-67) available from AMERCHOL; POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

In other embodiments, the quaternary ammonium compound may be chosen from a quaternary ammonium salt and a quaternary diammonium salt.

Suitable examples of quaternary ammonium salts are tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethyl-ammonium methosulfate or distearoylethylhydroxyethylammonium methosulfate, or else, lastly, palmitylamidopropyltrimethylammonium chloride or stearamidopropyl-dimethyl(myristyl acetate) ammonium chloride, sold under the name Ceraphyl® 70 by the company Van Dyk.

Other types of quaternary ammonium salts for use according to the invention are quaternary ammonium salts of imidazoline, di- or triquaternary ammonium salts, and quaternary ammonium salts containing one or more ester functions.

Examples of quaternary ammonium salts that may especially be mentioned include:
those corresponding to the general formula below:

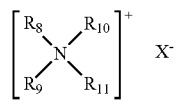

in which the groups R8 to R11, which may be identical or different, represent a linear or branched aliphatic group containing from 1 to 30 carbon atoms, or an aromatic group such as aryl or alkylaryl, at least one of the groups R8 to R11 denoting a group containing from 8 to 30 carbon atoms, preferably from 12 to 24 carbon atoms. The aliphatic groups may comprise heteroatoms such as, in particular, oxygen, nitrogen, sulfur and halogens. The aliphatic groups are chosen, for example, from C1-30 alkyl, C1-30 alkoxy, polyoxy(C2-C6)alkylene, C1-30 alkylamide, (C12-C22)alkylamido(C2-C6)alkyl, (C12-C22)alkylacetate and C1-30 hydroxyalkyl; X— is an anion chosen from the group of halides, phosphates, acetates, lactates, (C1-C4)alkyl sulfates, and (C1-C4)alkyl- or (C1-C4)alkylaryl-sulfonates.

Among the quaternary ammonium salt, those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds;

quaternary ammonium salts of imidazoline, for instance those of the formula below:

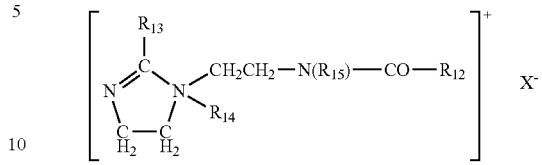

in which R12 represents an alkyl or alkenyl group containing from 8 to 30 carbon atoms, derived for example from tallow fatty acids, R13 represents a hydrogen atom, a C1-C4 alkyl group or an alkyl or alkenyl group containing from 8 to 30 carbon atoms, R14 represents a C1-C4 alkyl group, R15 represents a hydrogen atom or a C1-C4 alkyl group, X— is an anion selected from the group consisting of halides, phosphates, acetates, lactates, alkyl sulfates, alkylsulfonates or alkylarylsulfonates in which the alkyl and aryl groups each preferably comprise from 1 to 20 carbon atoms and from 6 to 30 carbon atoms. R12 and R13 preferably denote a mixture of alkyl or alkenyl groups comprising from 12 to 21 carbon atoms, for example tallow fatty acid derivatives, R14 denotes a methyl group, and R15 denotes a hydrogen atom. Such a product is sold, for example, under the name Rewoquat® W 75 by the company Rewo;

quaternary diammonium or triammonium salts, in particular of the following formula:

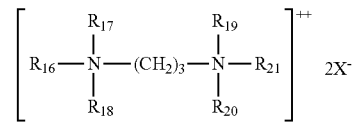

in which R16 denotes an alkyl radical containing approximately from 16 to 30 carbon atoms, which is optionally hydroxylated and/or interrupted by one or more oxygen atoms, R17 is selected from hydrogen and an alkyl radical containing from 1 to 4 carbon atoms or a group (R16a)(R17a)(R18a)N—(CH2)3, R16a, R1m, R18a, R18, R19, R20 and R21, which are identical or different, are selected from hydrogen and an alkyl radical containing from 1 to 4 carbon atoms, and X— is an anion selected from the group of halides, acetates, phosphates, nitrates and methyl sulfates. Such compounds are, for example, Finquat CT-P, available from the company Finetex (Quaternium 89), and Finquat CT, available from the company Finetex (Quaternium 75), quaternary ammonium salts containing at least one ester function, such as those of the formula below:

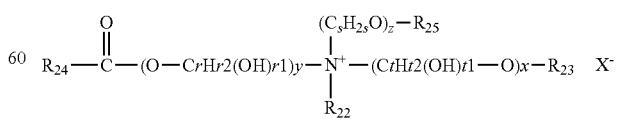

in which:
R22 is selected from C1-C6 alkyl groups and C1-C6 hydroxyalkyl or dihydroxyalkyl groups;

R23 is selected from:
the group

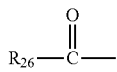

groups R27, which are linear or branched, saturated or unsaturated C1-C22 hydrocarbon-based groups,
a hydrogen atom,
R25 is selected from:
the group

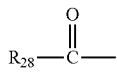

groups R29, which are linear or branched, saturated or unsaturated C1-C6 hydrocarbon-based groups,
a hydrogen atom,
R24, R26 and R28, which are identical or different, are selected from linear or branched, saturated or unsaturated C7-C21 hydrocarbon radicals;
r, s and t, which may be identical or different, are integers ranging from 2 to 6;
r1 and t1, which may be identical or different, are equal to 0 or 1, and r2+r1=2r and t1+t2=2t,
y is an integer ranging from 1 to 10;
x and z, which may be identical or different, are integers ranging from 0 to 10;
X— is a simple or complex, organic or inorganic anion;
with the proviso that the sum x+y+z is from 1 to 15, that when x is 0, then R23 denotes R27 and that when z is 0, then R25 denotes R29.

The alkyl groups R22 may be linear or branched, and more particularly linear.

Preferably, R22 denotes a methyl, ethyl, hydroxyethyl or dihydroxypropyl group, and more particularly a methyl or ethyl group.

Advantageously, the sum x+y+z is from 1 to 10.

When R23 is a hydrocarbon-based group R27, it may be long and may have 12 to 22 carbon atoms, or may be short and may have from 1 to 3 carbon atoms.

When R25 is a hydrocarbon-based group R29, it preferably contains 1 to 3 carbon atoms.

Advantageously, R24, R26 and R28, which may be identical or different, are chosen from linear or branched, saturated or unsaturated C11-C21 hydrocarbon-based groups, and more particularly from linear or branched, saturated or unsaturated C11-C21 alkyl and alkenyl groups.

Preferably, x and z, which may be identical or different, are equal to 0 or 1.

y is advantageously equal to 1.

Preferably, r, s and t, which may be identical or different, equal 2 or 3, and even more particularly are equal to 2.

The anion X— is preferably a halide (chloride, bromide or iodide) or an alkyl sulfate, more particularly methyl sulfate. However, it is possible to use methanesulfonate, phosphate, nitrate, tosylate, an anion derived from an organic acid, such as acetate or lactate, or any other anion that is compatible with the ammonium containing an ester function.

The anion X— is even more particularly chloride or methyl sulfate.

Use is made more particularly, in the composition according to the invention, of the ammonium salts of formula (XII) in which:
R22 denotes a methyl or ethyl group,
x and y are equal to 1;
z is equal to 0 or 1;
r, s and t are equal to 2;
R23 is selected from:
the group

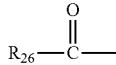

methyl, ethyl or C14-C22 hydrocarbon-based groups,
a hydrogen atom,
R25 is selected from:
the group

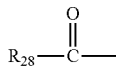

a hydrogen atom,
R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups.

The hydrocarbon-based groups are advantageously linear.

Mention may be made, for example, of the compounds such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, of triisopropanolamine, of an alkyldiethanolamine or of an alkyldiisopropanolamine, which are optionally oxyalkylenated, with C10-C30 fatty acids or with mixtures of C10-C30 fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a dimethyl or diethyl sulfate), methyl methanesulfonate, methyl para-toluenesulfonate, glycol chlorohydrin or glycerol chlorohydrin.

Such compounds are sold, for example, under the names DEHYQUART by the company Henkel, STEPANQUART by the company STEPAN NOXAMIUM by the company Ceca or REQOQUAT WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the quaternary ammonium salts containing at least one ester function, which can be used, it is preferred to use dipalmitoylethylhydroxyethylmethylammonium salts.

In preferred embodiments, the quaternary ammonium compound of the present invention is chosen from polyquaternium-6, polyquaternium-10, polyquaternium-67, and mixtures thereof.

In other preferred embodiments, the quaternary ammonium compound of the present invention is chosen from polyquaternium-6, polyquaternium-67, and mixtures thereof.

In yet preferred embodiments, the quaternary ammonium compound of the present invention is chosen from polyquaternium-6.

In the present invention, the quaternary ammonium compound may be employed in the composition of the present invention in an amount of from about 0% to about 10% by weight, preferably from about 0.1% to about 8% by weight, preferably from about 0.5% to about 5% by weight, preferably from about 0.75% to about 4%, preferably from about 1% to about 3% by weight, based on the weight of the composition as a whole, including all ranges and subranges within these ranges.

In certain embodiments, the quaternary ammonium compound is selected from Polyquaternium-6, Polyquaternium-10, and Polyquaternium-67, and is employed in the composition of the present invention in an amount of about 0.5%, or about 1%, or about 1.25%, or about 1.5%, or about 1.75%, or about 2%, or about 2.25%, or about 2.5%, or about 2.75%, or about 3%, or about 3.25%, or about 3.5%, or about 3.75%, or about 4%, or about 4.25%, or about 4.5% by weight, based on the total weight of the composition.

In other embodiments, the quaternary ammonium compound is not present in the inventive composition.

Water

The compositions of the present invention contain water. Water can be present in the amount of about 95%, 92%, 90%, 89%, 88%, 87%, 85%, 84%, 83%, 82%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 90% by weight, or from about 60% to about 88% by weight, relative to the weight of the compositions.

In other embodiments, water can be present in the compositions of the present invention in the amount of at least about 95%, 92%, 90%, 89%, 88%, 87%, 85%, 84%, 83%, 82%, 80%, 70%, 60%, 50%, 40%, 30%, 20%, 10%, 5% by weight or less, based on the total weight of the compositions.

Cosmetically Acceptable Solvent

The compositions of the present invention may further comprise at least one cosmetically acceptable solvent chosen from organic solvents.

Suitable organic solvents may be chosen from volatile and nonvolatile organic solvents.

Suitable organic solvents are typically C2-C8 alcohols, glycols, polyols, polyol ethers, glycol ethers, glycerin, hydrocarbons, oils, and mixtures thereof. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL™ DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluoro oils such as nonafluoromethoxybutane and perfluoro-methylcyclopentane.

The amount of the organic solvent/compound present in the compositions of the present invention can range from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-between, relative to the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-between, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 mono-alcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In certain embodiments of the present invention, the at least one organic solvent is chosen from ethanol.

Intermediate Agent

The intermediate agent of the present invention may be any shampoo or conditioner composition. Preferably, the intermediate agent has a neutral pH.

Auxiliary Ingredients

The compositions according to the invention may further comprise any auxiliary ingredient usually used in the field under consideration, selected, for example, from conditioning agents, natural and synthetic oils, humectants, shine agents, fillers, colorants, pigments, chelating agents, sequestering agents, fragrances, preservatives, stabilizers, and mixtures thereof.

It is a matter of routine operations for a person skilled in the art to adjust the nature and amount of the additives present in the compositions in accordance with the invention such that the desired cosmetic properties and stability properties thereof are not thereby affected.

pH

In certain embodiments, the neutralizing agent is used in an amount such that the pH of the compositions of the invention is from about pH 2 to less than about 7, preferably, from about pH 2 to about 6.5, or more preferably from about pH 2 to about 6 or from about pH 2 to about 4, including all ranges and subranges there-between.

In some embodiments, the neutralizing agent is used in an amount such that the pH of the compositions of the invention is from about 2 to 6, including all ranges and subranges there-between.

In other embodiments, the neutralizing agent is used in an amount such that the pH of the compositions of the invention is from about 2 to 4, including all ranges and subranges there-between.

In certain other embodiments, the pH of the compositions of the invention is about 2, 2.5, 3, 3.5, 4, 4.5, 5, 5.5, 6, 6.5.

pH can be adjusted with acidic agents other than the thiol-based reducing agents of the invention such as mineral acids, chlorhydric acid or phosphoric acid, or with basic agents such as mineral basic agents as ammonia, carbonates, bicarbonates, hydroxides or organic basic agents such as alcanolamines.

All numbers expressing pH values are to be understood as being modified in all instances by the term "about" which encompasses up to +/−0.2. For example, a pH value of about 7.0 refers to 7+/−0.2.

The compositions of the present invention are prefereably in the form of an emulsion, for example, oil-in-water emulsion and water-in-oil emulsion.

In other embodiments, the composition of the present invention has a viscosity of from about 60 M2 to about 70 M2, preferably from about 62 M2 to about 68 M2, more preferably from about 62 M2 to about 65 M2, as measured by a Rhéomat RM180 at 25° C.

In certain preferred embodiments, the composition of the present invention has a viscosity of from about 62 M2 to about 65 M2 and a pH ranging from about pH 2 to about 6.

In some preferred embodiments, the composition of the present invention has a viscosity of from about 62 M2 to about 65 M2 and a pH ranging from about pH 2 to about 4.

All numbers expressing viscosity values are to be understood as being modified in all instances by the term "about" which encompasses up to +/−0.2. For example, a viscosity value of about 64.2 M2 refers to 64.2+/−0.2 M2.

In preferred embodiments, the composition of the present invention is a hair straightening composition.

The composition of the present invention is stable such that the straightening efficacy of the composition is preserved until the composition is ready to be used.

In addition, the compositions of the present invention did not exhibit phase separation.

Methods of Making

The compositions of the present invention are made by combining at least one reducing agent, at least one neutralizing agent, at least two fatty substances, at least one alkoylated fatty alcohol, optionally at least one quaternary ammonium compound, and water.

In one embodiment, the method of making the compositions of the present invention comprises the steps of:

(1) combining:

(a) least one reducing agent selected from thiol reducing agents, non-thiol reducing agents, and mixtures thereof;

(b) at least one neutralizing agent;

(c) at least two fatty substances comprising:

i. a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and ii. a second fatty substance selected from fatty alcohols;

(d) at least one nonionic surfactant selected from alkoxylated fatty alcohol and alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;

(e) optionally, at least one quaternary ammonium compound; and (f) water;

all weights being based on the total weight of the composition; and (2) mixing (a) to (f) in order to form a composition having a pH ranging from 2 to less than 7.

The invention also concerns a process of shaping or altering the shape of hair, for example, by straightening hair. The process comprises the steps of:

(1) applying onto the hair, a composition containing:

(a) least one reducing agent selected from thiol reducing agents, non-thiol reducing agents, and mixtures thereof, preferably selected from thiolactic acid, thioglycolic acid, and mixtures thereof, and more preferably selected from thiolactic acid;

(b) at least one neutralizing agent, preferably selected from aminomethyl propanol, monoethanolamine, sodium hydroxide, and mixtures thereof;

(c) at least two fatty substances comprising:

i. from about 1% to about 60% by weight of a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and ii. from about 5% to about 10% by weight of a second fatty substance selected from fatty alcohols;

(d) from about 2.5% to about 6% by weight of at least one alkyl(ether)phosphate selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof; and (e) water;

all weights being based on the total weight of the composition;

wherein the pH of the composition ranges from 2 to less than 7.

(2) brushing the hair;

(3) heating the hair at a temperature of at least 40° C., preferably at a temperature of from about 40° C. to about 250° C., preferably from about 100° C. to about 230° C., or more preferably from about 150° C. to about 230° C.; while optionally applying a smoothing action on the hair, wherein when a smoothing action is employed, the heating action and smoothing action are accomplished by use of a heating flat iron device; and (4) rinsing the hair with water or contacting the hair with an intermediate agent having a neutral pH, followed by rinsing with water.

Preferably, before the composition in the process above is applied onto the hair, the hair is first contacted with a shampoo having a neutral pH and then rinsed with water.

In certain embodiments, the intermediate agent in the process above is a shampoo or conditioner, preferably having a neutral pH.

In certain embodiments, the composition is allowed to remain (leave-on time) on the keratin fibers for a pre-determined amount of time, for example, from about 1 to about 60 minutes, or such as from about 5 to about 45 minutes, or such as from about 5 to about 30 minutes, or such as from about 10 to about 20 minutes, or such as at about 20 minutes, or such as at about 10 minutes. The pre-determined amount of time is sufficient to achieve satisfactory straightening or shaping or altering the shape of the keratin fibers such as hair on the human head.

In other embodiments, the composition is rinsed from the hair with water before brushing the hair. The rinsed hair may also be subjected to a detangling or smoothing action before brushing the hair.

Suitable devices for detangling or brushing or smoothing the hair include a hair brush, comb, or heating flat iron. The smoothing or detangling action on the hair may also include running the fingers through the hair.

The composition can also be applied onto the hair using an applicator device or with the hands or gloved hands.

A suitable applicator device is an applicator brush or applicator comb or applicator spatula or a dispenser or applicator tip attached to the container holding the composition.

Heat (at a temperature of at least 40° C.) can be applied to the hair while the smoothing action is performed on the hair. The heat source can be chosen from a blow dryer, a flat iron, a hair dryer, a heat lamp, a heat wand, or other similar devices.

In addition, independently of the embodiment use, the composition present on the fibers or hair is left in place for a time, generally, from about 1 minute to about 60 minutes, such as from about 5 minutes to about 45 minutes, or such as from about 5 minutes to about 20 minutes, or such as from about 10 minutes to about 20 minutes, or such as of about 20 minutes or such as of about 10 minutes.

It has been surprisingly and unexpectedly discovered that the compositions of the present invention have a non-drip consistency that is still easy to spread on keratin fibers, such as hair.

It has surprisingly and unexpectedly discovered that the application of the composition onto the fibers results in satisfactory straightening of hair.

The straightening effects obtained using the compositions and process of the present disclosure may also be durable or wash resistant.

The degree of straightening the hair may be evaluated by visually assessing the reduction in curliness and/or waviness and/or frizziness of the hair after contacting the hair with the composition of the invention. Another type of evaluation can also involve measuring the length of the hair as well as the width of the bulk of hair before and after contacting the hair with the composition.

It was surprisingly and unexpectedly discovered that the hair contacted with the compositions of the invention did not feel as rough and visually appeared to be more smooth, extended and straight compared to hair contacted with conventional or traditional straightening compositions.

The compositions of the present invention may be packaged in any suitable container such as a tube, a jar or a bottle. In certain embodiments, the composition can be packaged in a tube or bottle, for example, a squeeze tube or squeeze bottle. Additionally, an applicator device can be attached or connected to the opening of the packaging/squeeze tube or bottle wherein the applicator device is a brush or a comb with teeth such that the ends of the teeth have openings from which the composition of the invention can flow through and be applied directly onto the hair.

The composition of the present invention may also be provided as component of a kit for shaping or altering the shape of hair wherein the kit can additionally contain other components such as an intermediate agent having a neutral pH chosen from a shampoo or a conditioner.

As used herein, the process and composition disclosed herein may be used on the hair that has not been artificially dyed, pigmented or permed.

As used herein, the process and composition disclosed herein may be also used on the hair that has been artificially dyed, pigmented or permed.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

Examples

The following Examples are intended to be non-restrictive and explanatory only, with the scope of the invention being defined by the claims.

The ingredient amounts in the compositions/formulas described below are expressed in % by weight, based on the total weight of the composition/formula.

Example 1: Compositions

TABLE 1

Inventive Composition (Emulsion)

| INCI US | Formula A, % by weight | RM code |
| --- | --- | --- |
| ETHANOLAMINE | 3 | 671 |
| THIOLACTIC ACID | 8 | 2004 |
| POLYQUATERNIUM-6 | 1 | 52762 |
| POLYQUATERNIUM-67 | 0.1896 | 79120 |
| PPG-5-CETETH-20 | 3 | 53031 |
| MINERAL OIL | 43.1 | 145 B |
| AMODIMETHICONE | 1.15 | 75110 |
| CETETH-10 PHOSPHATE | 1.75 | 71969 |
| CETEARYL ALCOHOL | 8.25 | 71969 |
| WATER | Q.S. to 100 | |

TABLE 2

Inventive Composition (Emulsion)

| INCI US | Formula B, % by weight | RM code |
| --- | --- | --- |
| AMINOMETHYL PROPANOL | 3 | 1690 |
| THIOLACTIC ACID | 8 | 2004 |
| POLYQUATERNIUM-6 | 1 | 52762 |
| PPG-5-CETETH-20 | 2.1 | 53031 |
| MINERAL OIL | 2.1 | 145 B |
| CETETH-10 PHOSPHATE | 0.875 | 71969 |
| CETEARYL ALCOHOL | 7.525 | 71969 |
| WATER | Q.S. to 100 | |

The compositions above were each prepared according to the general procedure:

2. Heat water to about 60° C.

3. Add the PPG-5-ceteth-20 and keep the temperature at about 60° C. and agitate the mixture for 10 minutes.

4. Combine Ceteth-10 Phosphate, Cetearyl alcohol, Polyquaternium-67 (if present), and Mineral Oil and mix for another 25 minutes at 60° C. and add to PPG-5 cetheth-20 and water mixture.

5. If present, stir Polyquaternium-6 for 10 minutes at 40° C. and add to resulting mixture.

6. Combine the neutralizing agent at 25° C. with agitation and then add the thiolactic acid.

7. Adjust the pH and check the viscosity.

The viscosity of the inventive composition was measured using the Mettler RM 180 Rheomat, viscometer spindle #2, at 25° C. (uD=Units of Deflection).

A viscosity measurement in M2 units ranging up from about 60 to 65 M2 corresponded to a texture and consistency of an emulsion or cream composition. The cream texture provided the benefits of ease of application of the composition into the hair, spreadability of the composition on the hair, and/or ease of brushing or combing the hair. The inventive composition with the cream texture also did not readily drip off the hair contacted with the composition and remained on the hair during the straightening processing time.

The consistency and texture of the inventive formulas allow for the formulas to be packaged jars, in tubes (e.g., squeeze tubes) or bottles (eg, applicator bottles).

The inventive formula was also found to be stable. Stability was measured by placing the formulas in a humidity-controlled environment set at 4° C., 25° C. and 45° C. for at least 2 months. The formula was considered to be stable when no phase separation is observed and there were very little fluctuations in viscosity and pH.

Example 2: Processes for Straightening or Altering the Shape of Hair and Assessments of Straightening Performance Processes for Straightening Hair These studies were conducted on curly or wavy hair swatches (virgin hair, i.e., not chemically treated) using the inventive compositions.

The process of straightening the hair was performed according to a rinsing protocol (Process 1) and a non-rinsing protocol (Process 2).

For Process 1, the following steps were followed:

1. the hair was contacted with a shampoo (neutral pH);
2. the hair was rinsed with water and blow dried;

3. the inventive composition was applied onto the hair using an applicator brush device (approximately 1 gram of the composition per gram of hair or approximately 300 grams per head of hair);

4. the inventive composition was allowed to remain on the hair for thirty minutes;

5. the inventive composition was rinsed off the hair;

6. the hair was brushed with a hair brush using 20 to 30 strokes;

7. the hair was smoothed and heated with a flat iron set at 230° C. and using 10 strokes (or passes);

8. the hair was contacted with a shampoo and/or a conditioner (neutral pH);

9. the hair was rinsed with water (if shampoo is used in step 7, then this rinsing step can optionally, be followed by a step of contacting the hair with a conditioner having neutral pH, and then rinsing with water);

10. the shampoo/rinse/optional conditioning/rinse cycle was repeated as many times as desired.

For Process 2, the following steps were followed:

1. the hair was contacted with a shampoo (neutral pH);

2. the hair was rinsed with water and blow dried;

3. the inventive composition was applied onto the hair using an applicator brush device (approximately 1 gram of the composition per gram of hair or approximately 300 grams per head of hair);

4. the inventive composition was allowed to remain on the hair for thirty minutes;

5. the hair was brushed with a hair brush using 20 to 30 strokes;

6. the hair was smoothed and heated with a flat iron set at 230° C. and using 10 strokes (or passes);

7. the hair was contacted with a shampoo and/or a conditioner (neutral pH);

8. the hair was rinsed with water; (if shampoo is used in step 7, then this rinsing step can optionally be followed by a step of contacting the hair with a conditioner having neutral pH, and then rinsing with water);

9. the shampoo/rinse/optional conditioning/rinse cycle was repeated as many times as desired.

Assessments of Straightening Performance and Reduction of Frizziness and Volume of Hair Straightening performance on hair was visually assessed for the following attributes: reduction of the volume (width) of the hair (also indicative of the degree of frizziness of and degree of discipline of the hair) and degree of straightening of the hair swatch. These attributes can also be measured or assessed on a 1 to 4 scale, with 4 being the smallest volume which indicates the greatest degree of straightening or lengthening of the hair, greatest reduction in frizziness or volume of the hair and greatest amount of discipline of the hair.

The Figure shows images of images of hair swatches before treating the swatch with the inventive composition, formula B, after treating a swatch with formula B by subjecting the swatch to the above-described rinsing protocol (process 1), and after treating a swatch with formula B by subjecting the swatch to the above-described non-rinsing protocol (process 2), It was found that the inventive formula significantly straightened the hair from a curly state, imparted excellent discipline to the hair (i.e., very low amount of or no frizz) and significantly reduced the volume of the hair.

The hair swatch subjected with formula B and the rinsing protocol (process 1) had a measurement of 4, which indicated the greatest degree of straightening and reduction of frizziness to the hair. The hair swatch subjected with formula B and the non-rinsing protocol (process 2) had a measurement of 3, which also showed a significant degree of straightness and reduction of frizziness in comparison to the hair swatch before treatment.

Example 3: Testing Various Ingredients Employed in the Inventive Formula

A. Testing different neutralizing agents (sodium hydroxide and aminomethyl propanol) in aqueous solutions containing 8% by weight thiolactic acid at different pH values on curly or wavy hair swatches (virgin hair, i.e., not chemically treated) using Process 1.

TABLE 3

| Sodium Hydroxide | | | | | | |
|---|---|---|---|---|---|---|
| | pH value | | | | | |
| | 2 | 4 | 6 | 8 | 10 | 12 |
| % by wt of sodium hydroxide | 0.2 | 2.0 | 3.0 | 3.8 | 4.4 | 6.3 |
| Straightening performance | 3.5 | 3.5 | 3.5 | 2.0 | — | — |

At pH values of 8 to 12, a high level of sensitization was observed; hair breakage was also observed in this pH range. As such, the hair was not rated for straightening performance at pH values of 10 and 12. At pH values of 2 to 6, hair cosmeticity and discipline was improved.

TABLE 4

| Aminomethyl Propanol | | | | | | |
|---|---|---|---|---|---|---|
| | pH value | | | | | |
| | 2 | 4 | 6 | 8 | 10 | 12 |
| % by wt of Aminomethyl Propanol | 0.3 | 4.6 | 6.5 | 7.0 | 15.8 | 30.0 |
| Straightening performance | 3.5 | 3.5 | 1.5 | 2.5 | — | — |

At pH values of 6 to 12, a high level of sensitization was observed; hair breakage was also observed in this pH range. The hair was not rated for straightening performance at pH values of 10 and 12. At pH values of 2 to 4, hair cosmeticity and discipline was improved; the hair also felt natural to the touch.

B. Swatch evaluation using different concentrations of Thiolactic acid in aqueous solutions having similar pH values on curly or wavy hair swatches (virgin hair, i.e., not chemically treated).

TABLE 5

| Thiolactic Acid | | | |
|---|---|---|---|
| | pH value | | |
| | 3.51 | 3.54 | 3.51 |
| % by weight thiolactic acid | 4 | 6 | 8 |
| % by wt of sodium hydroxide | to pH | to pH | to pH |
| Straightening performance | 3.0 | 3.5 | 4.0 |

From the table above, it was found that at similar pH values, the degree of straightening increased as the level of thiolactic acid increased.

C: Swatch evaluation using two different cellulose compounds as viscosity/thickening agent in aqueous on curly or wavy hair swatches (virgin hair, i.e., not chemically treated).

It is to be understood that the foregoing describes preferred embodiments of the invention and that modifications may be made therein without departing from the spirit or scope of the invention as set forth in the claims.

The invention claimed is:

1. A composition in the form of an emulsion for straightening hair comprising:
    (a) from 1% to 15% by weight, based on the total weight of the composition, of at least one reducing agent selected from thiolactic acid, thioglycolic acid, salts thereof, and mixtures thereof;
    (b) from 0.1% to 6.3% by weight, based on the total weight of the composition, of at least one neutralizing agent;
    (c) at least two fatty substances comprising:
        i. a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and
        ii. a second fatty substance selected from fatty alcohols;
    (d) at least one nonionic surfactant selected from alkoxylated fatty alcohols and alkyl(ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;
    (e) optionally, at least one quaternary ammonium compound; and
    (f) water;
        wherein the pH of the composition ranges from 2 to 5.5.

2. The composition, according to claim 1, wherein the at least one neutralizing agent is selected from organic amines, alkali metal hydroxides, alkali earth metal hydroxides, alkali metal carbonates, alkali metal phosphates, and mixtures thereof.

3. The composition, according to claim 1, wherein the at least one neutralizing agent is selected from aminomethyl propanol, sodium hydroxide, potassium hydroxide, lithium hydroxide, aminomethyl propanediol, triisopropanol amine, dimethylstearylamine, dimethyl/tallowamine, lysine, ornithine, arginine, monoethanolamine, triethanolamine, calcium hydroxide, calcium bicarbonate, and mixtures thereof.

4. The composition, according to claim 1, wherein the at least one neutralizing agent is aminomethyl propanol and is present in an amount of from 0.1% to 6.3% by weight, based on the total weight of the composition.

5. The composition, according to claim 1, wherein the at least one neutralizing agent is sodium hydroxide and is present in an amount of from 0.1% to 4.1% by weight, based on the total weight of the composition.

6. The composition, according to claim 1, wherein the at one least neutralizing agent is monoethanolamine and is present in an amount of from 0.1% to 4.1% by weight, based on the total weight of the composition.

7. The composition according to claim 1, wherein the first fatty substance is selected from paraffin oils, petroleum jelly, liquid paraffin, polydecenes, hydrogenated polyisobutene, perfluoromethylcyclopentane, perfluoro-1,3-dimethylcyclohexane, dodecafluoropentane, mineral oil, hexane, dodecane, isohexadecane, isodecane, sunflower oil, maize oil, soya oil, cucurbit oil, grapeseed oil, sesame oil, hazelnut oil, apricot oil, macadamia oil, arara oil, sunflower oil, castor oil, avocado oil, jojoba oil, shea butter oil and mixtures thereof.

8. The composition according to claim 7, wherein the first fatty substance is present in an amount of from 1% to 60% by weight, based on the total weight of the composition.

9. The composition according to claim 1, wherein the second fatty substance is selected from cetyl alcohol, stearyl alcohol, cetearyl alcohol, oleyl alcohol, lauryl alcohol, behenyl alcohol, linoleyl alcohol, and mixtures thereof.

10. The composition according to claim 9, wherein the second fatty substance is present in an amount of from 2% to 20% by weight, based on the total weight of the composition.

11. The composition according to claim 1, wherein the optionally at least one quaternary ammonium compound is selected from polyquaternium-6, polyquaternium 10, polyquaternium-67, and mixtures thereof.

12. The composition according to claim 1, further comprising:
    at least one organic solvent selected from C2-C8 alcohols, glycols, polyols, polyol ethers, glycol ethers, glycerin, hydrocarbons, oils, and mixtures thereof and/or
    (ii) at least one auxiliary ingredient selected from conditioning agents, natural and synthetic oils, humectants, shine agents, fillers, colorants, pigments, chelating agents, sequestering agents, fragrances, preservatives, stabilizers, and mixtures thereof.

13. The composition of claim 1, wherein the pH ranges from 2 to 5.

14. The composition of claim 1, wherein the pH ranges from 2 to 4.

15. A composition for straightening hair comprising:
    (a) from 3% to 10% by weight of least one reducing agent selected from thiolactic acid, salts thereof, and mixtures thereof;
    (b) from 0.2% to 5% by weight of at least one neutralizing agent selected from organic amines, alkali metal hydroxides, alkali earth metal hydroxides, alkali metal carbonates, alkali metal phosphates, and mixtures thereof;
    (c) at least two fatty substances comprising:
        i. from 2% to 45% by weight of mineral oil;
        ii. from 3% to 10% by weight of cetearyl alcohol;
    (d) from 2% to 10% by weight of at least one alkyl(ether) phosphate chosen from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;
    (e) from 0.5% to 3% by weight of at least one quaternary ammonium compound selected from polyquaternium-6, polyquaternium-10, polyquaterium-67, and mixtures thereof; and
    (f) water;
        all weights being based on the total weight of the composition;
        wherein the pH of the composition ranges from 2 to 5; and
        wherein the composition is an emulsion.

16. A process for shaping hair or altering the shape of hair, the process comprising the steps of:
    (a) applying onto hair, a composition in the form of an emulsion containing:
        i. from 1% to 15% by weight, based on the total weight of the composition, of at least one reducing agent selected from thiolactic acid, thioglycolic acid, salts thereof, and mixtures thereof;
ii. 0.1% to 6.3% by weight, based on the total weight of the composition, of at least one neutralizing agent;
iii. at least two fatty substances comprising
  (1) a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and
  (2) a second fatty substance selected from fatty alcohols;
iv. at least one nonionic surfactant selected from alkyl (ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;
v. optionally, at least one quaternary ammonium compound; and
vi. water;
  wherein the pH of the composition ranges from 2 to 5.5;
(b) brushing the hair;
(c) heating the hair at a temperature of at least 40° C.; while optionally applying a smoothing action on the hair; and
(d) rinsing the hair with water or contacting the hair with an intermediate agent having a neutral pH and selected from a shampoo and/or a conditioner, followed by rinsing with water.

17. The process according to claim 16, wherein after applying the composition on the hair according to step (a), the process further comprises a step of leaving the composition in step (a) on the hair for a period of time of 5 to 30 minutes before brushing the hair according to step (b).

18. A method of making a composition in the form of an emulsion for shaping or altering the shape of hair, the method comprising:
(1) combining:
  (a) from 1% to 15% by weight, based on the total weight of the composition, of least one reducing agent selected from thiolactic acid, thioglycolic acid, salts thereof, and mixtures thereof;
  (b) 0.1% to 6.3% by weight, based on the total weight of the composition, of at least one neutralizing agent selected from organic amines, alkali metal hydroxides, alkali earth metal hydroxides, and mixtures thereof;
  (c) at least two fatty substances comprising:
    i. a first fatty substance selected from alkanes, esters of fatty acid, esters of fatty alcohol, hydrocarbons, silicones, non-silicone waxes, mineral oils, vegetable oils, non-silicone synthetic oils, and mixtures thereof; and
    ii. a second fatty substance selected from fatty alcohols;
  (d) at least one nonionic surfactant selected from alkyl (ether)phosphates selected from PPG-5-Ceteth-10 phosphate, Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate and mixtures thereof;
  (e) optionally 0.5% to 5% by weight of at least one quaternary ammonium compound selected from polyquaternium-6, polyquaternium-10, polyquaternium-67, and mixtures thereof; and
  (f) water;
  all weights being based on the total weight of the composition; and
(2) mixing (a) to (f) in order to form a composition having a pH ranging from 2 to 5.5.

* * * * *